United States Patent
Bernatoniene et al.

(10) Patent No.: US 11,654,175 B2
(45) Date of Patent: May 23, 2023

(54) *ELSHOLTZIA CILIATA* ESSENTIAL OIL EXTRACT AS ANTIARRHYTHMIC DRUG

(71) Applicant: LIETUVOS SVEIKATOS MOKSLŲ UNIVERSITETAS, Kaunas (LT)

(72) Inventors: Jurga Bernatoniene, Kaunas (LT); Lauryna Pudziuvelyte, Kaunas (LT); Jonas Jurevicius, Kaunas (LT); Regina Macianskiene, Kaunas (LT); Sandrita Simonyte, Kaunas (LT)

(73) Assignee: LIETUVOS SVEIKATOS MOKSLU UNIVERSITETAS, Kaunas (LT)

( * ) Notice: Subject to any disclaimer, the term of this patent is extended or adjusted under 35 U.S.C. 154(b) by 16 days.

(21) Appl. No.: 16/982,769

(22) PCT Filed: Apr. 6, 2018

(86) PCT No.: PCT/IB2018/052396
§ 371 (c)(1),
(2) Date: Sep. 21, 2020

(87) PCT Pub. No.: WO2019/193400
PCT Pub. Date: Oct. 10, 2019

(65) Prior Publication Data
US 2021/0008141 A1 Jan. 14, 2021

(51) Int. Cl.
A61K 36/53 (2006.01)
A61K 47/26 (2006.01)
A61K 9/00 (2006.01)
A61K 9/107 (2006.01)

(52) U.S. Cl.
CPC ............ *A61K 36/53* (2013.01); *A61K 47/26* (2013.01); *A61K 9/0053* (2013.01); *A61K 9/107* (2013.01)

(58) Field of Classification Search
None
See application file for complete search history.

(56) References Cited

FOREIGN PATENT DOCUMENTS

| CN | 1481789 A | 3/2004 |
|---|---|---|
| CN | 101181418 A | 5/2008 |
| CN | 104857393 A | 8/2015 |
| CN | 105381402 A | 3/2016 |
| CN | 107334813 A | 11/2017 |
| DE | 102005060880 A1 | 6/2007 |

OTHER PUBLICATIONS

Sun et al. (CN104027390A Machine Translation) (Year: 2014).*
Liu et al. (CN104622954A Machine Translation) (Year: 2015).*
Heilongjiang Jiangheng Pharmaceutical Science & Tech Co Ltd (CN105381402A Machine Translation) (Year: 2016).*
Hu et al. (CN101306080A Machine Translation) (Year: 2007).*
International Search Report for PCT/IB2018/052396 dated Dec. 12, 2018 (three pages).
Guo et al., "Elsholtzia: phytochemistry and biological activities", Chemistry Central Journal, Biomed Central Ltd., vol. 6, No. 1, pp. 1-8, Dec. 2012.
Tian Guang-Hui, "Chemical Constituents in Essential Oils from Elsholtzia ciliata and Their Antimicrobial Activities", Chinese Herbal Medicines, 5(2), pp. 104-108, Jan. 2013.
Seungwon Shin, "Study on Activities of the Essential Oil from Elsholtzia ciliata against Some Antibiotic-Susceptible and Resistant Strains of Pathogenic Bacteria", Yakhak Hoeji, vol. 54, No. 2, pp. 122-125, Feb. 2010.
Pudziuvelyte et al., "Different extraction methods for phenolic and volatile compounds recovery from Elsholtzia ciliata fresh and dried herbal materials", Industrial Crops and Products, vol. 120, pp. 286-294, May 2018.
Haiyun et al., "Protective effect of total flavones from Elsholtzia blanda (TFEB) on myocardial ischemia induced by coronary occlusion in canines", Journal of Ethnopharmacology 94 (2004), pp. 101-107, Apr. 2004.

* cited by examiner

*Primary Examiner* — Robert A Wax
*Assistant Examiner* — Quanglong N Truong
(74) *Attorney, Agent, or Firm* — Tutunjian & Bitetto, P.C.

(57) ABSTRACT

The present invention provides a new formulation which includes *Elsholtzia ciliata* Extract. Experiments have shown that ECE decreases the rate of depolarization of upstroke of myocardial action potential, slows the propagation of electrical excitation and distributes the ECG QRS range, i.e. treats the heart as a first-class anti-arrhythmic drug. Due to its herbal origin, the ECE can be well tolerated and widely used as a safe drug for eliminating cardiac arrhythmias.

4 Claims, No Drawings

ELSHOLTZIA CILIATA ESSENTIAL OIL EXTRACT AS ANTIARRHYTHMIC DRUG

TECHNICAL FIELD

The present disclosure relates to new formulation of essential oil from *Elsholtzia ciliata* Extract (ECE). The present invention also relates to a method for preparation of formulation comprising the ECE essential oil as well as to the use of this essential oil in the treatment and prevention of arrhythmias in mammalians, particular in humans.

BACKGROUND

In recent years, the use of various herbs and/or herbal medical products for e prevention of disease, alleviating the effects thereof, or for treating diseases have been gradually increasing.

Cardiovascular disease is the most common cause of death, most of these deaths are due to cardiac arrhythmias. Only a rhythmic work of heart ensures a complete human life and physical activity. However, often, due to various reasons, the heart rhythm is disrupted, while the full-fledged human activity also fails. In clinical practice, various anti-arrhythmics are used to help eliminate cardiac arrhythmias. Due to different electrophysiological properties, antiarrhythmics are divided into five classes.

Patent application CN101181418 relates to a drug combination which cures arrhythmia and a production method. The drug combination is produced by red ginseng, epimedium, fructus psoraleae (stir-frying with salt-water) medlar, ma-huang, asarum, salvia miltiorrhiza and bloodsucker. The granule types comprise grain granule, hard capsule granule, soft capsule granule, troche, drop pill, pill and oral liquid preparation.

Patent application CN107334813 discloses an *Elsholtzia blanda* extract as well as a preparation method and applications of the *Elsholtzia blanda* extract. All-grass of *Elsholtzia blanda* is used as the raw material. The effective part, namely, total phenolic acid is prepared through the operation steps of extracting, concentrating, acidifying, filtering, column adsorption and the like. The phenols acids are mixed at a specific ratio in the *Elsholtzia blanda* extract, thus the obvious effects of removing oxygen radicals, resisting platelet aggregation, resisting myocardial ischemia, resisting arrhythmia, resisting inflammation, reducing the myocardial infarction area index and the like are achieved. The *Elsholtzia blanda* extract can be conveniently prepared into various oral or injection dosage forms for preventing and/or treating coronary heart diseases.

DE102005060880 describes a preparation of special extracts for use as an anti-arrhythmic agents in cardiac arrhythmia and for the improvement of coronary perfusion. The method comprises extracting the part of the plant *Leonurus cardiaca* by gradual extraction or hydrophilically with aqueous extraction using strong apolar solvent. Independent claims are included for: (1) a special extract of *Leonurus cardiaca*, obtained by the above method; and (2) a medicament comprising a special extract from the *Leonurus cardiaca* and further pharmaceutical compatible auxiliary material.

Patent application CN 104857393 provides a pharmaceutical preparation for treating arrhythmia. The pharmaceutical preparation is prepared from the following raw materials in parts by weight: 15 parts of oriental sesame seeds, 16 parts of conespike flemingia leaves, 20 parts of indocalamus leaf base, 18 parts of ovalleaf aspidistra rhizome, 15 parts of fir bark, 20 parts of sevanlobed nightshade herbs or fruits, 15 parts of sheathstipe greenbrier tubers and roots, 20 parts of divaricate knotweed roots, 14 parts of wrinkled *Elsholtzia* and 20 parts of roundpod jute leaves.

CN1481789 describes extract from *Elsholtzia* herb which is mixed with supplementary material in the ratio of 60-99 to 1-40 to prepare the medicine. The medicine is used in treating cardiac vascular diseases, such as myocardial ischemia, arrhythmia and hyperlipemia; eye diseases, such as hemorrhage of the ocular fundus caused by diabetes and hypertension, keratitis, conjunctivitis, climacteric syndrome, osteoprosis and neurodegeneration disease. It has also the functions of stopping cough, eliminating phlegm, resisting capillary blood vessel brittleness and abnormal penetration, inhibiting tumor cell, etc.

Compared with available technology, described preparation has simple and reasonable recipe, high curative effect, no toxic side effect, and different preparation forms for wide application. The invention aims at providing a drug curing the arrhythmia, not only has accurate curative effects, but also better improves clinic symptoms, shortens the treatment period and prevents recrudescence.

SUMMARY OF THE INVENTION

The main objective of the present invention is to provide a new formulation which comprises *Elsholtzia Ciliata* Extract. Experiments have shown that ECE decreases the rate of depolarization of upstroke of myocardial action potential, slows the propagation of electrical excitation and distributes the ECG QRS range, i.e. treats the heart as a first-class anti-arrhythmic drug. Due to its herbal origin, the ECE can be well tolerated and widely used as a safe drug for eliminating cardiac arrhythmias.

The main objective of the present invention is to provide a new formulation which comprises an herbal extract composition comprising aromatic aniseed grass essential oil which has been prepared from *Elsholtzia cilliata* herb; emulsifier Tween® 20; and purified water.

According to this main object, formulations according to the present invention are suitable for treatment, prevention of for use in the treatment or prevention of cardiac arrhythmic disease, wherein said cardiac arrhythmic disease is cardiac tachycardia which is related with the extrasystoles formed in the ventricles, as well as tachycardia due to the circulation of the pulse in the ventricles.

The herbal extract composition comprises 10-80 mL of aromatic aniseed grass essential oil, 10-80 ml emulsifier Tween® 20 and 20-80 mL purified water.

The herbal extract composition is prepared as pharmaceutical formulation or medicinal product in the form of emulsion, tablet or capsule.

Another object of the present invention is to provide a method by which special first-class anti-arythmic drug is produced.

A method for preparing the herbal extract composition is as follows: extracting dried leaves of *Elsholtzia cilliata* herb by hydrodistillation. Mixing an amount of 10-80 ml of said *Elsholtzia cilliata* oil extract with 10-80 ml emulsifier Tween® 20. After thoroughly mixing 20-80 mL pure water are added and again mixing.

Many antiarrhythmics are used in clinical practice. ECE is distinguished by the fact that it is of vegetable origin, and therefore it can be a safe, well tolerated antiarrhythmic drug.

Knowing that cardiac arrhythmias are very diverse, a new effective antiarrhythmic drug such as ECE can be used to eliminate some arrhythmias, such as ventricular tachyarrhythmias.

The preparation is effective in removing various forms of ventricular tachycardia. It is effective in blocking the extrasystoles formed in the ventricles, as well as tachycardia due to the circulation of the pulse in the ventricles.

DETAILED DESCRIPTION OF THE EMBODIMENTS

It has been found that a previously unknown special extract can be produced by the method described, which actually has significant cardiac effects and is suitable for suppressing cardiac arrhythmias and for improving coronary perfusion. This is described in more detail below.

A yellow, colored essential oil with a specific odor was produced from the dried aroma aniseed grass raw material—*Elsholtzia cilliata* (Thunb.) Hylander belonging to the family of Lamiaceae by hydrodistillation. For this purpose was used the Clevenger type hydrodistillation apparatus. Thirty grams of dried powdered *E. ciliata* herbal material was mixed with 500 mL purified water and submitted to hydrodistillation (temperature 120±2° C.). Duration of hydrodistillation is 3 hours.

After chemical analysis of essential oil, using the gas chromatography-mass spectrometry method, the main chemical compounds, namely elsholtzia monoterpenes and dehydroelsholtzia ketones, which comprise respectively 14.58% and 78.28% by weight based on total weight of essential oil composition, and sesquiterpenes (4.99%), of which are determined beta-bourbonenes, beta-cubes, isocariophilins, lindens, germakren D, trans-alpha-bergamotine, alpha-farnesen, gamma-cadinin, delta-cadinin.

Oral Solution—Emulsion

An emulsion which consists of flavoring anion essential oil, Tween® 20 emulsifier and distilled water was produced.

The aromatic aniseed grass essential oil of 40 mL is mixed with emulsion Tween® 20 of 40 mL, All components are fine mixed up. Then purified water of 20 mL is added. The resulting liquid is thoroughly mixed until a homogeneous, volatile solution (emulsion) is obtained.

The mixture was stirred for about 2-3 min using magnetic stirrer.

The invention claimed is:

1. A method for treating a human patient for cardiac arrythmias comprising the steps of:
    extracting dried leaves of *Elsholtzia ciliata* herb by hydrodistillation;
    mixing an amount of 10-80 ml of said *Elsholtzia ciliata* oil extract with 10-80 ml emulsifier polysorbate 20;
    adding 20-80 mL pure water and mixing to form an anti-arrythmic composition; and
    administering the anti-arrythmic composition to the human patient for treating and preventing cardiac arrhythmias.

2. The method of claim 1, wherein e step of mixing to perform the anti-arrythmic composition is performed for about 2 minutes to 3 minutes using a magnetic stirrer.

3. The method of claim 1, wherein the step of extracting comprises mixing 30 grams of dried powdered *Elsholtzia ciliata* herbal material with 500 mL of purified water to form a mixture, and subjecting the mixture to hydrodistillation.

4. The method of claim 3, wherein the hydrodistillation is performed at a temperature of 120±2° C. for a duration of 3 hours.

* * * * *